United States Patent [19]
Lambert et al.

[11] Patent Number: 5,262,645
[45] Date of Patent: Nov. 16, 1993

[54] SENSOR FOR MEASURING ALCOHOL CONTENT OF ALCOHOL GASOLINE FUEL MIXTURES

[75] Inventors: David K. Lambert, Sterling Heights; Stephen J. Harris, Bloomfield Village; Stephen J. Swarin, Rochester, all of Mich.

[73] Assignee: General Motors Corporation, Detroit, Mich.

[21] Appl. No.: 754,475

[22] Filed: Sep. 3, 1991

[51] Int. Cl.⁵ ............................................. G01N 21/35
[52] U.S. Cl. ..................................... 250/339; 250/341
[58] Field of Search ................ 250/339, 340, 341, 352, 250/345, 346

[56] References Cited

U.S. PATENT DOCUMENTS

| | | |
|---|---|---|
| 3,696,247 | 10/1972 | McIntosh et al. |
| 4,541,272 | 9/1985 | Bause ........................ 73/118 |
| 4,594,968 | 6/1986 | Degobert et al. ................... 123/1 A |
| 4,770,129 | 9/1988 | Miyata et al. ...................... 123/1 A |

FOREIGN PATENT DOCUMENTS

| | | | |
|---|---|---|---|
| 0304230 | 2/1989 | European Pat. Off. ........... | 250/339 |
| WO90/03565 | 4/1990 | PCT Int'l Appl. | |

*Primary Examiner*—Janice A. Howell
*Assistant Examiner*—Richard Hanig
*Attorney, Agent, or Firm*—George A. Grove

[57] ABSTRACT

An alcohol sensing device is provided for determining the alcohol content within an alcohol/gasoline fuel mixture provided to an internal combustion engine. The sensing device uses infrared spectrometry measuring techniques. The infrared sensing device determines the ratio of light absorption by the alcohol/gasoline mixture at two discrete wavelengths within the near-infrared spectrum. The two particular wavelengths of interest are preferably chosen so that at one of the infrared wavelengths, alcohol is strongly absorbing while the gasoline exhibits very little absorption, and at the second wavelength both the alcohol and the gasoline exhibit are essentially non-absorbing. A light beam is transmitted through the alcohol/gasoline fuel mixture such that the two discrete wavelengths traverse the same optical path. A first and second detector are adjacently disposed so as to receive the emitted light from each wavelength after their transmission through the alcohol/gasoline fuel mixture. A third and fourth detector are adjacently disposed in proximity to the first and second detectors for sensing the drift in ambient temperatures corresponding to the first and second detectors. Once the signals corresponding to the two wavelengths are obtained and the signals corresponding to the ambient temperatures are factored out, the ratio of the absorbances by the fuel mixture at both wavelengths is computed. From this ratio and the fuel temperature the concentration of alcohol in the fuel is determined.

17 Claims, 2 Drawing Sheets

SENSOR FOR MEASURING ALCOHOL CONTENT OF ALCOHOL GASOLINE FUEL MIXTURES

This invention generally relates to a sensor for detecting the alcohol concentration within an alcohol-containing gasoline fuel mixture supplied to an automotive internal combustion engine. More particularly, this invention relates to an alcohol sensor which determines the alcohol concentration within such a fuel mixture using infrared spectroscopy, wherein a light beam emitted at near-infrared wavelengths is transmitted through the fuel mixture and the ratio of infrared absorbances by the mixture at two discrete wavelengths is determined.

BACKGROUND OF THE INVENTION

Automobiles which can operate on alternative fuels, such as arbitrary mixtures of alcohol and gasoline, are indicative of future trends and, in fact, will soon be required by law in certain regions. For proper engine operation it will be necessary to measure the ratio of alcohol-to-gasoline within the fuel mixture which is being injected into the combustion chamber. Since the automobile may be filled with gasoline at one instance and an alcohol-containing gasoline mixture of up to about 85% methanol at the next, this ratio is likely to change between fill-ups. Further, because alcohol and gasoline can physically separate in the gas tank, this ratio may continuously vary during the operation of the automobile. Therefore, it is necessary that this ratio be continuously monitored to assure proper operation of the automobile's engine.

A variety of techniques have been previously proposed for making these on-board measurements of the alcohol content within the fuel mixture for control of the engine parameters. Typically, these methods have measured various properties of the gasoline mixture, including the dielectric constant, thermal conductivity, index of refraction, change in the speed of sound through the mixture and microwave absorption. However, these methods tend to be prohibitively expensive for widespread use or the measuring techniques involved are inherently problematic since they tend to be strongly dependent on temperature and/or the detailed properties of the gasoline used. Further, as an exacerbation of these shortcomings, the composition of a particular gasoline mixture may vary considerably even within a single name brand. Therefore, these methods have failed to provide the reliability required for automotive engine control applications.

An alcohol sensing device based on infrared spectroscopy methods would generally avoid the problems associated with these previous methods, including the strong dependence on temperature and/or the gasoline composition. This is because infrared spectroscopy is an analytical technique which measures the relative absorption of various infrared wavelengths by a particular specimen and is thereby dependent on the molecular constitution of the specimen. A sensor for determining the alcohol content in gasoline which utilizes such an infra-red absorption technique is disclosed in U.S. Ser. No. 07/699,018 filed May 13, 1991 in the name of Harris et al and assigned to the assignee of the present invention overcomes many of the problems cited above. Harris et al disclose an alcohol sensing device which utilizes infrared spectroscopy measuring techniques capable of detecting alcohols without any interference from the presence or absence of gasoline.

The Harris device contains a single light source which emits a spectrum of light including the near-infrared wavelengths. The sensor measures the ratio of light transmission (or conversely—light absorption by the fuel mixture) at two discrete wavelengths within the near-infrared spectrum. Alcohols will generally absorb different wavelengths of light as compared to alcohol-free gasolines because the alcohols contain oxygen-hydrogen (O—H) bonds while gasolines practically have no O—H bonds.

Therefore, Harris et al teach the selection of two particular wavelengths such that at one of the infrared wavelengths, alcohol is strongly absorbing because of the vibrational overtone transition associated with the O—H bond in the alcohol molecule. At this same wavelength however, the gasoline is more transparent, i.e., exhibits very little absorption, since O—H bonds are almost entirely absent from gasoline. The second wavelength is chosen so that both the alcohol and the gasoline exhibit little absorption of the infrared wavelength and are therefore nearly transparent.

During operation of the Harris device, a beam of light is emitted which contains the two discrete wavelengths within the near infrared spectrum. The light beam is transmitted such that the two discrete wavelengths traverse the same optical path. Two detectors are adjacently disposed so as to receive the emitted light after transmission through the alcohol/gasoline fuel mixture.

The first detector determines the amount of infrared absorbance by the fuel mixture at the first wavelength by filtering all other wavelengths except the first wavelength of interest. Similarly, the second detector determines the amount of infrared absorbance by the fuel mixture at the second wavelength. The two detectors are thermopile detectors which convert the received light into heat. Accordingly each of the two thermopile detectors generates an increase in temperature corresponding to the amount of transmitted light received at the two particular wavelengths. The temperature increases are then converted by thermopiles into voltage signals which are readily measured.

Once these signals for the two wavelengths are obtained, the ratio of the amounts of absorption by the alcohol/gasoline fuel mixture at both wavelengths can be computed. However, in order to obtain an adequate signal-to-noise ratio, the light source taught by Harris et al must be alternated between a high power and low power setting. The reason for this is that excessive thermal "noise" would otherwise be fed into the computation of the alcohol-gasoline ratio based upon the light received by the two thermopiles. As an example, the ambient temperature of the thermopiles will likely differ, i.e., drift, with respect to time during the operation of the engine. Because a thermopile converts temperature difference into a voltage output, all thermal sources to which the thermopile is exposed will influence its voltage output, whether the source is the intended light source or the temperature of the substrate to which the thermopile is secured, as will be discussed more fully later.

As a result, though this type of device taught by Harris et al utilizes infrared absorption spectroscopy, it is still strongly dependent on temperature stability due to the nature of its detection system. This dependency has a particularly adverse effect in an environment such as that of automobiles. Within the engine environment of an automobile, temperatures may fluctuate greatly over a wide range from about −40° C. up to about 120°

C., making it difficult in practice to maintain the two thermopiles of this device at constant temperatures throughout the operation of the engine. If the ambient temperature drift is not compensated for, the absorbance measurements by the detectors will give erroneous results. Accordingly, these various thermal sources must all be accounted for in the algorithm used to determine the air-fuel ratio in order to ensure an accurate measurement.

With the above conditions in mind, the shortcomings of the Harris device may be more fully explained as follows. The voltage output of a thermopile may be represented by $V_o$ which is the sum of a voltage resulting from the energy absorbed from the light $V_s$ plus a voltage resulting from the ambient temperature influencing the thermopile $V_d$. By providing a high and low setting for the light source, two values for $V_s$ are obtained $-V_{sh}$ and $V_{sl}$, for the high and low settings, respectively—while $V_d$ remains essentially constant within any given cycle of the light source. The difference between the high and low setting voltage outputs $V_{oh}$ and $V_{ol}$ can now be determined as follows:

$$V_{oh} - V_{ol} = (V_{sh} + V_d) - (V_{sl} + V_d) = V_{sh} - V_{sl}$$

From the above it can be seen that the voltage output due to the ambient temperature of the substrate $V_d$ has been factored out of the equation. What is left is the difference between the voltage due solely to the modulation of the light source, $V_{sh} - V_{sl}$. By taking a ratio between the first and second thermopiles, or $(V_{sh} - V_{sl})_1 / (V_{sh} - V_{sl})_2$, an absolute value for the relative absorbances of the fuel at the two frequencies can be ascertained. The concentration of alcohol in the fuel is then determined from standard absorption data.

Though the device taught by Harris et al has been noted to perform well, certain disadvantages associated with the modulation of the light source have been identified. Obviously, the need to modulate the light source between a high and low intensity setting complicates the method of analyzing the fuel ratio, requiring an algorithm which controls the timing and intensities between the high and low settings. An additional disadvantage is that the response time of the sensor is slower as a result of the time required to heat and cool the filaments of the light source between settings so as to avoid errors in the thermopile outputs. As an example, the thermal decay time for the filaments used by Harris et al was approximately 200 milliseconds. This contrasts to the response time of approximately 28 milliseconds for the thermopile sensors themselves. Accordingly, the cycle time for the Harris device was not limited by the capability of the type of sensor used, but by the form of light source used.

Though light sources having substantially shorter thermal decay times may be appropriate under some circumstances, the harsh environment of the automobile severely limits the choices available for sensing the fuel ratio as described. Therefore, it would be desirable to provide an alcohol sensor for determining the alcohol content in a fuel mixture for use in an automobile environment, which utilizes infrared absorption spectroscopy techniques as previously disclosed by Harris et al, but which alleviates the shortcomings associated with the need to modulate the light source between a high and low intensity setting. In particular, it would be desirable to provide such an alcohol sensor which can operate satisfactorily with the light source emitting light at only one intensity while still being able to factor in ambient temperature effects and other extraneous external influences.

SUMMARY OF THE INVENTION

It is an object of the present invention to provide an alcohol sensing device for use in determining the alcohol content within an alcohol-containing gasoline mixture.

It is a further object of this invention that such an alcohol sensing device utilize infrared spectroscopy techniques for determination of the relative absorption by the alcohol/gasoline fuel mixture at two discrete near-infrared wavelengths.

It is still a further object of this invention that the alcohol sensing device transmit a single light beam through the alcohol/gasoline fuel mixture for incidence upon a single substrate having two adjacently disposed detectors which are each filtered to receive a corresponding one of the two near-infrared wavelengths.

It is yet another object of this invention that the alcohol sensing device utilize at least one additional sensor adjacent the two adjacently disposed detectors and on the same substrate to detect and compensate for the drift in ambient temperature of the detectors and therefore increase the device's signal-to-noise ratio without the need to modulate the single light beam.

In accordance with a preferred embodiment of this invention, these and other objects and advantages are accomplished as follows.

A sensing device is provided for determination of the alcohol content within an alcohol-containing gasoline mixture, wherein this fuel mixture is provided via a fuel carrying line to an internal combustion engine for operation of that engine. The alcohol sensing device of this invention utilizes infrared spectroscopy measuring techniques and is capable of detecting alcohols without any interference from the presence or absence of gasoline.

The alcohol sensing device contains a single light source which emits a spectrum of light including the near-infrared wavelengths. The sensor measures the ratio of light transmission (or conversely—light absorption by the fuel mixture) at two discrete wavelengths within the near-infrared spectrum. Alcohols will generally absorb different wavelengths of light as compared to alcohol-free gasolines because the alcohols contain oxygen-hydrogen (O—H) bonds while gasolines practically contain no O—H bonds. Therefore, the two particular wavelengths of interest are preferably chosen so that at one of the infrared wavelengths, alcohol is strongly absorbing because of the vibrational overtone transition associated with the O—H bond in the alcohol molecule. At this same wavelength however, the gasoline is more transparent, i.e., exhibits very little absorption, since the gasoline does not contain practically any O—H bonds The second wavelength is chosen so that both the alcohol and the gasoline exhibit little absorption of the infrared wavelength and are therefore nearly transparent.

As an illustrative example, the fundamental vibrational transition wavelengths in alcohols are in the range of 2.8-2.9 micrometers while the shortest wavelength in alcohol-free gasoline is about 3.2 micrometers. Vibrational overtone transitions, which are infrared absorbing, are at roughly half of these wavelengths, one-third of these wavelengths and so on. Therefore, the detection of the alcohol within the fuel mixture can be made at predetermined wavelengths without any interference or absorption by the gasoline, just by appropriately choosing those wavelengths of interest. Specifically, the alcohol sensor of this invention compares infrared light transmission between two preferred spectral bands, one centered at about 1.5 micrometers wavelength where absorption by only the alcohol occurs and the other at about 1.3 micrometers wavelength where virtually no absorption occurs.

During operation of the sensor, which will correspond with the operation of the internal combustion engine receiving the alcohol-containing gasoline mixture, the light source emits a beam of light which contains the two discrete wavelengths within the near infrared spectrum. The light beam is transmitted through the alcohol/gasoline fuel mixture which is being carried within the fuel line to the internal combustion engine, such that the two discrete wavelengths traverse the same optical path. Two detectors are adjacently disposed so as to receive the emitted light from each wavelength after their transmission through the alcohol/gasoline fuel mixture. At least a third sensing device, and preferable a fourth sensing device, is also disposed adjacent the first two detectors for purposes of detecting the drift in ambient temperature of the two detectors.

The first detector determines the amount of infrared absorbance by the fuel mixture at the first wavelength by filtering all other wavelengths except the first wavelength of interest. Similarly, the second detector determines the amount of infrared absorbance by the fuel mixture at the second wavelength. The two detectors are preferably thermopile detectors which convert the received light into heat. Accordingly each of the two thermopile detectors generates an increase in temperature corresponding to the amount of transmitted light received at the two particular wavelengths.

The third sensing device is also preferably a thermopile detector and located in close proximity to the first two thermopile detectors but is shielded from the transmitted light beam of the light source. As a result, the third detector is able to almost exclusively sense the drift in ambient temperature of the first two detectors. The voltage from each of the three thermopile detectors is then measured. Once the signals for the two wavelengths are obtained and compared to the signal for the ambient temperature, the ratio of the amounts of absorption by the alcohol/gasoline fuel mixture between the two wavelengths is computed. In comparing the signals of the first two detectors, it is preferable to provide a fourth additional detector for sensing the drift in ambient temperature so as to allow each light-sensing detector to be paired with an ambient temperature-sensing detector. The algorithm comparing the light and ambient temperature signals can then be simplified. In any event, the concentration of alcohol in the fuel is then determined from the wavelength absorption ratio from standard absorption data.

A few of the particularly advantageous features associated with the sensor of this invention, and with infrared spectroscopy measuring techniques generally, are that alcohol concentration in the fuel can be determined by detecting two wavelengths emitted by a single light source, and that the critical parameter being measured is the ratio of the relative absorbances at the two different wavelengths. Therefore, any degradation of the light source or the detector will equally affect the measurements for both wavelengths and will essentially cancel out in the final ratio determination.

A more particular advantage of the present invention is that all of the thermopile detectors are extremely small and are mounted on a much larger carrying substrate which serves, in part, as a heat sink. Therefore, all external temperature effects experienced by the detectors will be substantially identical for all of the detectors and the thermal "noise" of the substrate's temperature will accordingly cancel since the ambient temperature-sensing detector's signal will be factored out prior to determining the ratio between the two signals from the first two thermopile detectors.

Also, because the thermal noise is detected and cancelled by factoring in the signal from the ambient temperature-sensing thermopile detector, the light source need only operate at one intensity throughout the operation of the device, avoiding any requirement for modulation as practiced by the prior art. Lastly, the cycle time of the device is reduced, the complexity of the control for the device is simplified and the number of components within the device is minimized, which thereby tends toward an affordable sensor for automotive applications.

Other objects and advantages of this invention will be better appreciated from the detailed description thereof, which follows.

BRIEF DESCRIPTION OF THE DRAWINGS

The above and other advantages of this invention will become more apparent from the following description taken in conjunction with the accompanying drawing wherein.

DETAILED DESCRIPTION OF THE PREFERRED EMBODIMENTS

In accordance with this invention, an alcohol sensing device is provided for determining the alcohol content within an alcohol/gasoline fuel mixture which is being provided for the operation of an internal combustion engine. The sensing device uses infrared spectrometry measuring techniques and is capable of detecting the amount of alcohol without any interference from the presence of gasoline. The infrared sensing device determines the ratio of light transmission through the alcohol/gasoline mixture at two discrete wavelengths within the near-infrared spectrum.

Within the near-infrared wavelength range of about 1.2 to 2.4 micrometers (slightly longer wavelengths than visible light), absorption spectra for alcohol and gasoline are substantially different, making the near-infrared spectra particularly suited for these types of measurements. The alcohol, which may constitute up to 85% by volume of an alcohol/gasoline fuel mixture, is primarily in the form of either ethanol or methanol, while gasoline is a mixture of volatile hydrocarbons with the major components being branched-chain paraffins, cycloparafins and aromatics. Alcohol will absorb light at wavelengths which are different than alcohol-free gasoline because the alcohols contain oxygen-hydrogen (O—H) bonds while gasoline generally does not.

Preferably, the two particular wavelengths are chosen so that at the first wavelength the alcohol is strongly infrared-absorbing because of a vibrational overtone transition of the O—H bond within the alcohol molecule. At this same wavelength the gasoline which is characterized by a virtual absence of O—H bonds does not absorb and is correspondingly more transparent. At the second wavelength both alcohol and gasoline exhibit negligible absorption of the infrared wavelength and are therefore nearly transparent.

More specifically, the fundamental transition wavelengths in alcohols are in the range of 2.8–2.9 micrometers while the shortest wavelength in alcohol-free gasoline is about 3.2 micrometers. Overtone transitions which cause absorbance by the molecule occur at roughly half these wavelengths within the near-infrared spectrum, or about 1.4 and 1.6 micrometers respectively for the alcohol and the gasoline. Absorbing overtone transitions also occur at about one-third of these wavelengths, and could be determined if necessary by other means. Therefore, the detection of the alcohol can be made by measuring the absorbance at the particular wavelength without any interference or absorption by the gasoline.

Figure 1:
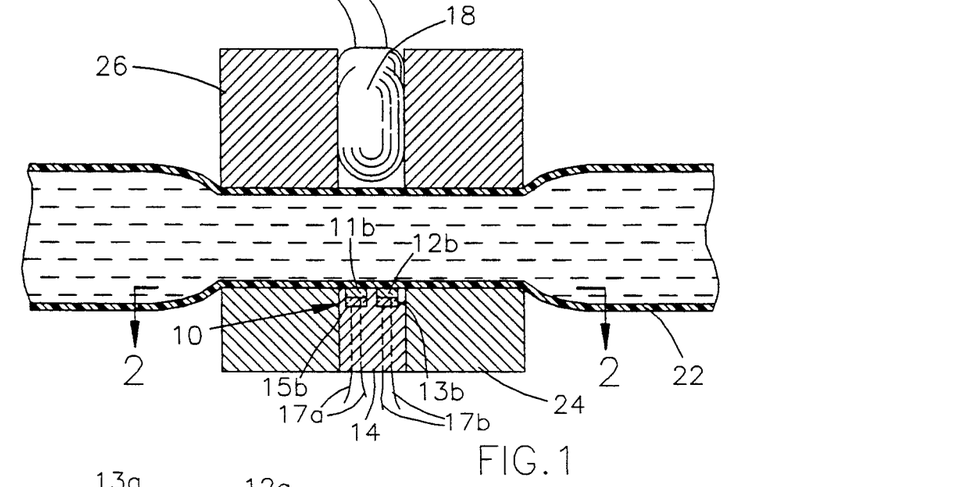
FIG. 1 is a cross-sectional view of the alcohol sensor in accordance with this invention for detection of the alcohol concentration within an alcohol/gasoline fuel mixture which is provided to an internal combustion engine via a fuel carrying line.

The alcohol sensing device of this invention is shown cross-sectionally in FIG. 1. The sensor basically consists of a single light source 18, a thermopile detector unit 10, and fixturing means 24 and 26 for retaining the light source 18 in a manner so that it transmits its emitted light through the fuel carrying line 22 to be incident upon the detector unit 10.

As shown, the sensor detects the alcohol content of the fuel mixture which is being carried within a fuel carrying line 22, such as for the operation of an internal combustion engine within an automobile. At the desired region where the alcohol detection is to occur, the conventional fuel line, which is typically a ⅜" diameter metal tube, is converted to a ⅜" diameter tube 22 of a suitable material which is transparent and chemically resistant to attack by alcohols and gasoline. (The diameter of the converted tubing is to be identical or compatible with the diameter of the conventional metal tubing used elsewhere in the fuel line, and is therefore dependent on the size of the fuel line tubing used.) The conversion between the metal fuel line and the transparent tubing 22, in the region where detection is to occur, is accomplished using conventional fittings (not shown).

A preferred material for the fuel carrying line 22 would be fluorinated ethylene polymers, such as the commercially available material Teflon, some forms of which are transparent at the wavelengths of interest and are chemically resistant to alcohols and gasoline. It is noted though that only the clear Teflon tubing was found to be suitable for the fuel line 22. The clear Teflon tubing 22 transmitted a much larger fraction of the infrared light than did white Teflon. For these reasons, the clear Teflon is most preferred. It is foreseeable that other suitable materials which are transparent to the desired wavelengths and also chemically resistant to the fuel mixture could be substituted.

In order to obtain the desired optical path length for transmission of the infrared wavelengths through the fuel mixture, the tubing 22 is compressed appropriately to form the desired path length in that region where detection will occur. It is to be noted that the preferred tubing 22 material is relatively easy to compress. As shown more clearly in FIG. 3, the tubing 22 is compressed as it passes through a gap 30 between two metal plates 24 and 26 which are attached to each other by four screws 28. The screws 28 allow the width of the gap 30 to be adjusted depending on the desired optical path length. The plates 24 and 26 are formed from any metal which will withstand the environmental extremes within the automobile while not being practically prohibitive. For demonstrational purposes, the plates 24 and 26 were formed from aluminum, however it is not necessary that they be formed from such material. In addition, one of the plates 26 was larger at about 25×32×22 millimeters than the other 24 which was about 25×32×7 millimeters, since the larger plate 26 held the light source 18. Actually, plates 24 and 26 are not necessary so long as some form of rigid fixturing means is provided.

Figures 2, 3:
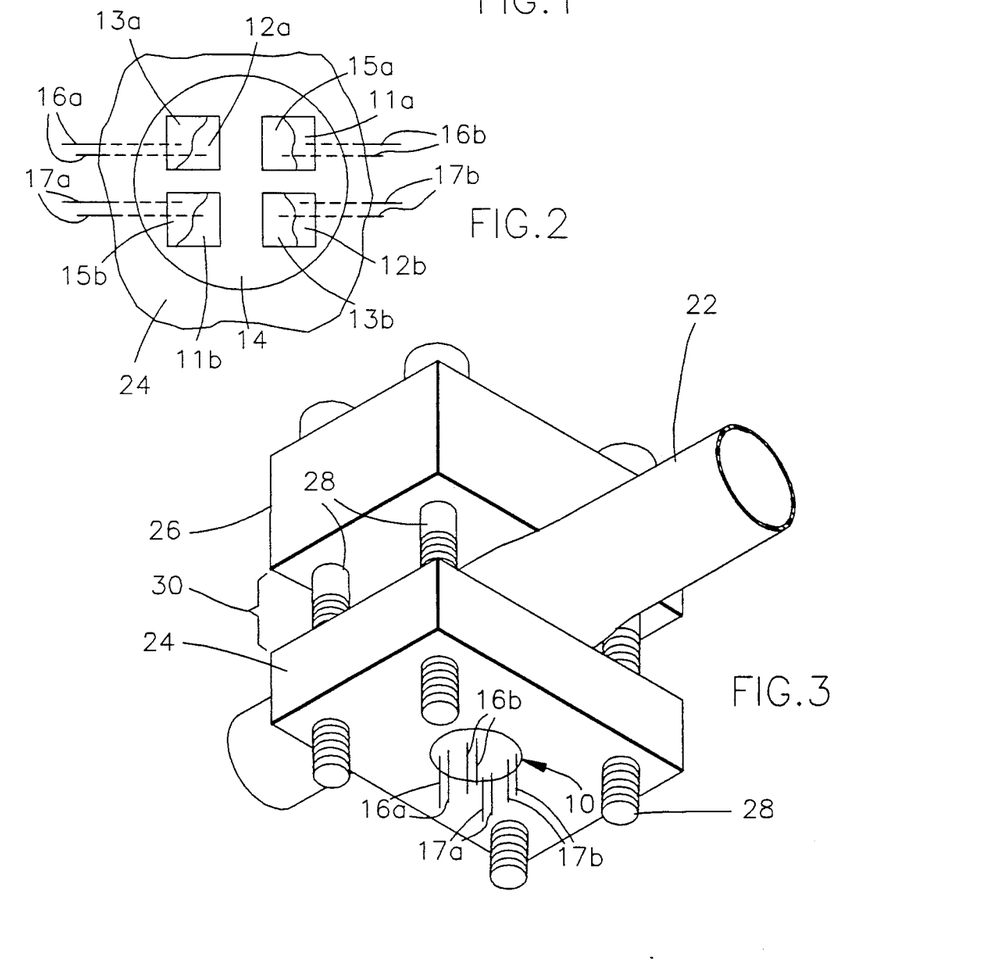
FIG. 2 is a plan view of four thermopile detectors provided on the carrying substrate shown in FIG. 1 for detection of the incident light at two discrete wavelengths and the ambient temperature of the substrate.
FIG. 3 is an elevated view of the alcohol sensor shown in FIG. 1.

The appropriate optical path length for transmission of the near-infrared wavelengths through the fuel mixture within the fuel line 22, (represented by the width of the gap 30 between metal plates 24 and 26 as shown in FIG. 2) should not be so large that it results in all of the transmitted light being absorbed by the fuel mixture within the fuel line 22. Nor should the optical path length 30 be so small that absorption is negligible. This determination of the appropriate path length will be discussed more fully later, yet optimum results appear to be realized with an optical path length 30 ranging between one and three millimeters for the wavelengths of interest.

Again as illustrated in FIG. 1, the sensor consists of a single light source 18, mentioned previously as being held within the larger aluminum plate 26. The single light source 18 emits white light at the near-infrared wavelengths of interest. The light source 18 is preferably a commercially available quartz-envelope tungsten-halogen light bulb. The preferred lamp 18 operates at a peak current of generally between 1.2 and 1.4 amps. Such bulbs can be expected to have maximum operating parameters up to 1.43 amps and 5 Volts. The preferred light bulb 18 can also be expected to have a life of approximately 5000 hours, thereby requiring few, if any, replacements during the life of the vehicle. It is preferred that the light bulb 18 is positioned so that the two detectors designated to sense the selected wavelengths (discussed more fully below) are illuminated to the same extent to reduce the effects of light scattering by the fuel mixture. This may require the further use of a diffuser.

Held within the smaller metal plate 24, is the thermopile detector unit 10, shown in both FIGS. 1 and 3. As more closely seen in FIG. 2, the detector unit 10 consists of four individual thermopile detectors 11a, 11b, 12a, and 12b provided on an appropriate substrate 14. External electrical connection wires 16a, 16b and 17a, 17b extend from each detector 11a, 11b, and 12a, 12b. As shown, detectors 12a and 11a are paired with wires 16a and 16b, respectively, and detectors 11b and 12b are paired with wires 17a and 17b, respectively. Generally, a thermopile detector contains many thermocouples which are electrically connected in series so that their individual voltages are cumulative. Such a thermopile detector can convert incident infrared light into heat, producing a voltage proportional to the resulting increase in temperature. The preferred thermopile detector unit 10 used in the specific embodiment of this invention was a pair of DR34 dual element thermopile detectors from Dexter Research Inc. of Dexter, Mich.

As shown in FIG. 2, the detector unit 10 contains four miniaturized multijunction thermopiles 11a, 11b, 12a and 12b. The four thermopiles 11a, 11b, 12a and 12b are each made from interdigitated thin films of evaporated bismuth and antimony. Two of the thermopiles 12a and 12b are covered with an energy absorbing smoke black film 13a and 13b. The smoke black film 13a and 13b absorbs spectral wavelengths from the ultraviolet to the far-infrared and is deposited onto the two interdigitated active junction areas (depicted as 12a and 12b) which are approximately 3.16 millimeters×0.4 millimeters×1.4 millimeters in volume, and which are separated from each other by a distance of about 0.5 millimeters.

The third and fourth thermopiles 11a and 11b are shielded by an opaque film 15a and 15b which substantially prevents any absorption of the light beam by the thermopiles 11a and 11b. Otherwise, the thermopiles 11a and 11b are identically sized and oriented with respect to the first and second thermopiles 12a and 12b. The four thermopile detectors 11a, 11b, 12a and 12b are hermetically sealed under a purged atmosphere of Argon or Nitrogen and appropriately heat treated to ensure long term stability. The final package for the detector unit 10 is resistant to both mechanical and temperature shock.

The thermopiles 11a, 11b, 12a and 12b are capable of operating within the temperature range experienced within an automobile engine compartment of about −40° C. and 120° C. and are also sufficiently sensitive and accurate over this temperature range in the acoustically noisy environment of the engine compartment. In addition, since the thermopiles 11a, 11b, 12a and 12b are voltage generating devices, they do not require application of a current or bias voltage for operation. They are also compatible with conventional electrical connections. Lastly and perhaps most significantly, the response of the thermopiles 11a, 11b, 12a and 12b is sufficiently close to being linear up to the maximum power that needs to be detected. Specifically, in the preferred embodiment the maximum optical power absorbed by the detector is approximately one milliWatt, giving a temperature rise of 3.1 degrees Centigrade. Detector response changes by about 0.004 per degree Centigrade, so at the maximum power level the detector is expected to deviate by a factor of about 0.012 from linear response. The effect of this non-linearity on sensor output is negligible. However, it is noted that over a large temperature range, such as over 100 degrees Centigrade, the sensor would become quite non-linear.

Figure 4:
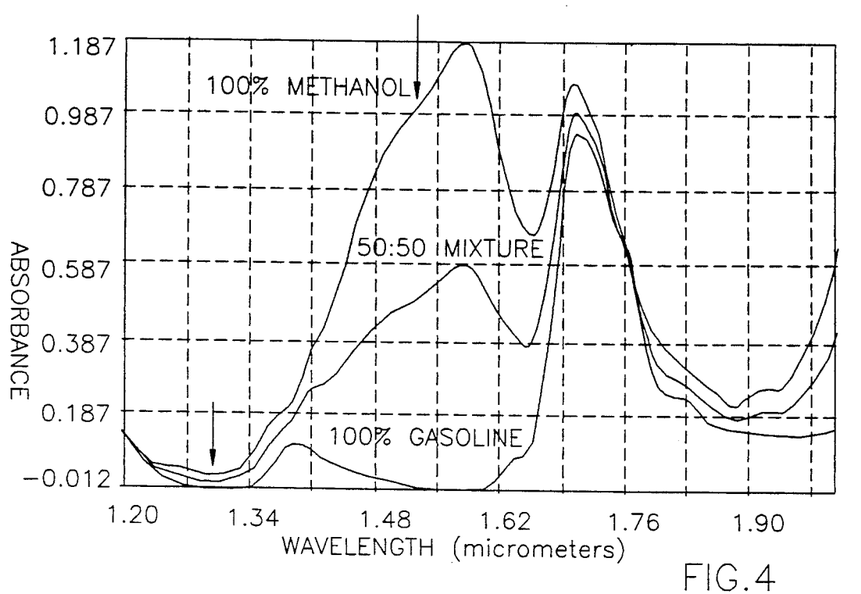
FIG. 4 is a graph showing relative absorbance versus near-infrared wavelength in micrometers, for 100% methanol, 100% gasoline and a 50:50 mixture of each.

As stated previously, the thermopile detectors 12a and 12b absorb the preferred wavelengths of interest with this invention. The alcohol sensor of this invention compares infrared light transmission between two preferred spectral bands, one centered at about 1.5 micrometers wavelength and the other at about 1.3 micrometers wavelength. As shown in the graph of FIG. 4, which depicts the relative absorbance at near-infrared wavelengths (in micrometers) for methanol, gasoline and a 50:50 mixture of each, there is a vibrational overtone transition of alcohol associated with the O—H molecular bonds which is centered at about 1.5 micrometers, at which the alcohol absorbs the infrared light and the gasoline does not. At about 1.3 micrometers, neither the alcohol or gasoline absorb much of the infrared light. The parameters which were considered for choosing the particular wavelengths of interest are discussed more fully later, however, it is important to note that these preferred wavelengths of 1.3 and 1.5 micrometers are within the range of absorbing wavelengths for the thermopiles 12a and 12b.

With this arrangement, it should be noted that it is also foreseeable that light could be detected at more than two wavelengths in order to gain more information about the fuel mixture, such as the temperature, octane number, boiling point or other parameters. This would best be accomplished by providing a fifth (or more depending upon the amount of information desired) thermopile element on the detector unit 10 which is filtered to receive a third wavelength of interest.

In addition, although the thermopile detectors 11a, 11b, 12a and 12b are most preferred, there are other types of infrared detectors that operate at 1.5 micrometers wavelength or less which could be suitable for this application. However, these alternative detectors are typically limited by their range of operational temperatures, sensitivity to vibration and noise, and/or cost, and therefore would not lend themselves to the widespread use envisioned by this invention. The thermopile detectors 11a, 11b, 12a and 12b appear to optimize these concerns and are therefore preferred.

Some of these alternative, but lesser preferred, detectors include the inexpensive type of PbS semiconductive devices. However, they are not designed to operate at the relatively high temperatures experienced within an engine compartment. In addition, semiconductor materials having an appropriate band gap and which use either a photoconductive or photovoltaic effect for sensing incident infrared light, such as $In_xGa_{1-x}As$ or $Hg_xCd_{1-x}Te$ materials, are more sensitive than thermopiles to infrared light at the lower end of the temperature range. However, as the temperature of the semiconductor material increases, sensitivity is reduced due to the thermally activated current within the semiconductor.

Another type of possible infrared detector which is similar to the thermopile detector (11a, 11b, 12a and 12b), in that it also converts infrared light into heat and then measures the resulting temperature increase, is the pyroelectric type of detector. Although pyroelectric detectors can be made to be as sensitive to incident light as thermopile detectors, they are not as suitable for use in acoustically and vibrationally noisy environments like the engine compartment of an automobile, since all pyroelectric materials are also piezoelectric which thereby results in a microphone effect when vibrated. For these various reasons, it is preferred to use thermopile detectors such as those previously described, as the infrared detectors.

To successfully use the thermopile detector unit 10 for measuring the alcohol content within a fuel mixture, the optical throughput to the light-detecting thermopiles 12a and 12b must be maximized. At the same time, the ambient temperature-detecting thermopiles 11a and 11b must be sufficiently isolated from the light source while maintaining intimate thermal proximity with the light-detecting thermopiles 12a and 12b. This is accomplished by choosing (1) an appropriate pair of optical filters 13a and 13b to filter the desired wavelengths of interest to the light-detecting thermopiles 12a and 12b, (2) an appropriate pair of opaque films 15a and 15b to block the light beam from being received by the ambient temperature-detecting thermopiles 11a and 11b, (3) a suitable optical path length (represented as gap 30) for transmission of the infrared light through the fuel within the fuel line 22, (4) an appropriate material for the transparent fuel line 22, (5) a suitable optical infrared light source 18 and (6) optimal relative positions between the light source 18 and the light-detecting thermopiles 12a and 12b.

Figure 5:
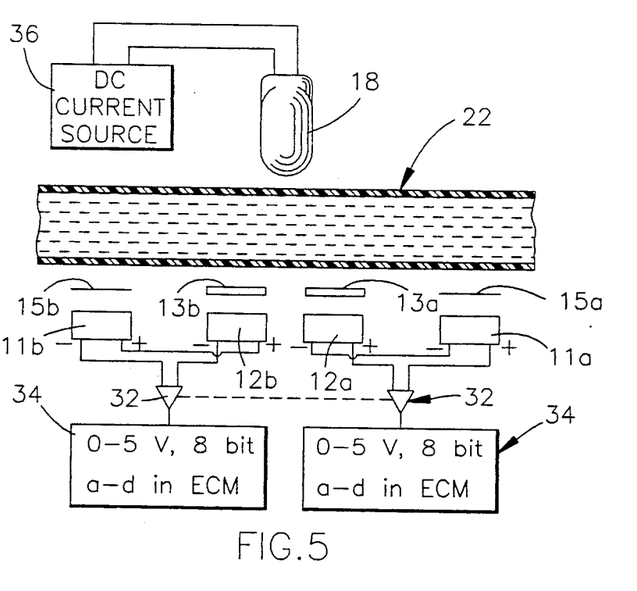
FIG. 5 is a schematic view of the electronic detection system used with the alcohol sensing device of this invention.

The next consideration is the electronic measuring circuitry. The preferred electronic measuring system performs as follows. The incandescent light bulb 18 is energized by a suitable current source 36 to emit a light beam. Concurrently, the corresponding dc voltages are generated by the temperature increase of the two light-detecting thermopiles 12a and 12b. The voltages are used to compute a ratio which is proportional to the ratio of the intensities of the transmitted light from the light source 18 at both chosen wavelengths of interest. This ratio can then be used to determine the alcohol content at a given temperature. For an extremely accurate sensor, a fuel temperature measurement or compensation is required and preferred, since the infrared absorption of alcohol in the 1.5 micrometer band is slightly temperature dependent. It is therefore desirable to measure the temperature of the fuel mixture with a separate thermistor or thermocouple.

The desired wavelengths of interest, which determined the particular optical filters 13a and 13b used, were chosen as follows. In order to obtain the required absorption measurements for each of the two discrete wavelengths, optical filters which permit transmission of only those desired wavelengths at each light-detecting thermopile 12a and 12b were necessary and installed onto the detecting areas of each thermopile 12a and 12b. In choosing the optical filter, the objective was to choose a filter which would result in the maximum degree of sensitivity for a corresponding change in the alcohol concentration within the fuel mixture.

According to our theoretical model, sensitivity to a change in the alcohol concentration was optimized by choosing a 1.5 micrometer filter that passed a band of wavelengths that was approximately the same as the alcohol spectral band in this wavelength region. This is a center wavelength of about 1.53 micrometers and transmission of light from about 1.43 to about 1.63 micrometers. As stated previously and as shown in FIG. 4, in this region identified by the right-most identifying arrow, the alcohol (methanol) is strongly infrared absorbing while the gasoline is not. A commercially available interference filter with approximately these optimum characteristics is Oriel Corporation's model 58045 with a center wavelength of 1.5 micrometers and 0.09 micrometer half band-width. A similar interference filter with a center wavelength of about 1.3 micrometers, Oriel model 58043, was used for the reference measurement wherein both the alcohol and the gasoline are non-absorbing, or relatively transparent, as identified in FIG. 4 by the left-most identifying arrow. The filters are interference filters, which reflect all wavelengths except the particular spectral band being filtered. The use of these two filters is preferred since they have comparable spectral transmission which helps limit problems of cross-talk between the two light-detecting thermopile detectors 12a and 12b.

Although the preferred wavelengths for measurement of absorbance are approximately 1.3 and 1.5 micrometers because at the first wavelength there is relatively no absorption by either component and strong absorption by only the alcohol at the second wavelength, it is clear from FIG. 4 that the wavelengths of interest could range between about 1.25 to 1.35 micrometers and between about 1.4 to 1.6, respectively.

Specifically the purchased optical filters were each circular, approximately 25.4 millimeters in diameter, and cut using a diamond saw to a rectangular piece of about $2 \times 4$ millimeters. Each of the rectangular filters 13a and 13b were permanently attached to a corresponding light-detecting thermopile 12a or 12b, so that each filter covered the sensitive area on its corresponding thermopile detector 12a or 12.

Our theoretical model was also utilized to determine the preferred optical path length (represented by gap 30) through the alcohol/gasoline fuel mixture. Generally, the model showed that for low concentrations of alcohol within the fuel mixture, i.e., less than 50% by volume alcohol, a long path length produces a high degree of sensitivity corresponding to a change in the alcohol concentration. However, at high concentrations of alcohol, i.e., greater than about 50% by volume alcohol, the sensitivity is diminished by a long path length. This is because much of the incoming infrared light is absorbed by the alcohol over the long path length.

Therefore, it was determined that the optimum path length 30 maximizes the change in light intensity per the change in the alcohol concentration at the maximum alcohol concentration, which is approximately 85% alcohol in the alcohol/gasoline mixtures. In practice, this optimum occurs when the incident light intensity for a maximum alcohol concentration of about 85% by volume is about 50% of the incident light intensity when the alcohol concentration is equal to zero.

Specifically, according to both this spread sheet model and experimental data, it was determined that with the 1.5 micrometer wavelength filter, (which is where alcohol is absorbing and gasoline is not) an optical path length of about one to three millimeters for transmission of the infrared light through the fuel mixture is optimum. In the actual embodiment, a path length 30 of approximately two millimeters was utilized. The optical path length 30 of two millimeters resulted in an incident light intensity, at an alcohol concentration of about 85% by volume, which was about half the intensity at an alcohol concentration of zero. It was further determined that, in general, the optimum optical path length 30 is inversely proportional to the maximum alcohol concentration which is to be measured. To form this preferred optical path length 30, of about two millimeters in the specific example, the fuel line 22 was compressed accordingly between the two metal plates 24 and 26, as shown in FIGS. 1 and 3.

In practice, it is noted that parameters which were not considered by the model affect the choice of filters 13a and 13b and path length 30. Stray light reaching each of the thermopile detectors 12a and 12b is one such consideration, such as from environmental light or when the emitted light is carried around the fuel line 22 by multiple reflections, thereby not passing through the fuel at all. The optical filters 13a and 13b also pass some of the emitted light which is outside of the desired band of frequencies. However, these problems are diminished as the amount of emitted light in the desired wavelength range is increased. Avoidance of these stray light effects is another reason for using the previously described preferred optical filter 13a and 13b, which has a relatively large bandwidth of about 0.2 micrometers and which therefore covers much of the alcohol absorption band.

In contrast to the filters 13a and 13b described above for the light-detecting thermopiles 12a and 12b, the ambient temperature-detecting thermopiles 11a and 11b must be completely shielded from the light beam emitted from the light source 18. As noted above, thermopiles 11a and 11b are shielded by suitable opaque films 15a and 15b which substantially prevent any absorption of the light beam. Accordingly, the temperature difference measured by both thermopiles 11a and 11b is due almost exclusively to the ambient temperature of the substrate 14. Otherwise, the ambient temperature-detecting thermopiles 11a and 11b are identically sized and oriented with respect to the light-detecting thermopiles 12a and 12b.

Once signals at two (or more) wavelengths are obtained the concentration of the alcohol within the alcohol/gasoline fuel mixture is determined as follows. The temperature of the fuel mixture is measured and the signals from the light-detecting thermopiles 12a and 12b and the ambient temperature-detecting thermopiles 11a and 11b are obtained. The signals resulting from the thermopiles 11a and 11b are then compared with the signals from the thermopiles 12a and 12b, respectively, to filter out the signal noise due to the influence of the ambient temperature of the substrate 14 on the light detecting thermopiles 12a and 12b. The differences between these signals are then appropriately ratioed to determine the transmitted intensity at each wavelength. The ratio is equal to the difference in voltage outputs corresponding to the thermopile 12a sensing transmission at the first wavelength and the thermopile 11a sensing the ambient temperature adjacent the thermopile 12a, divided by the difference in voltage outputs corresponding to the thermopile 12b sensing transmission at the second wavelength and the thermopile 11b sensing the ambient temperature adjacent the thermopile 12b. An illustrative equation is as follows:

$$R = (V_1 - V_3)/(V_2 - V_4).$$

where R is the ratio of absorbance, $V_1$ and $V_2$ are the voltage outputs by light-detecting thermopiles 12a and 12b sensing at first and second wavelengths, respectively, and $V_3$ and $V_4$ are the voltage outputs by the ambient temperature-detecting thermopiles 11a and 11b sensing the substrate's ambient temperature. $V_3$ and $V_4$ are nearly identical. The ratio is then compared to standard calibration curves for absorbance at that temperature.

Note that in order to determine the relative intensities it is not necessary that the two wavelengths are chosen such that only one of the components, i.e., the alcohol, absorbs at a particular wavelength, such as in the preferred embodiment. It is only necessary that the absorbances of gasoline and of the alcohol differ from each other at one of the two wavelengths. However, this latter mode of operation is less preferred, since with the preferred mode of measurement the relative measurements at the two wavelengths are more distinct because there is a clear absorption at one of the wavelengths which is attributable only to the one component.

In order to maximize the detected signal by the light-detecting thermopiles 12a and 12b, it was desirable to position the detector unit 10 close to the fuel line 22. The distance between the detector unit 10 and the clear tubing 22 may be adjusted by modifying the position of the detector unit 10 within the fixturing plate 24. By placing the detector 10 flush against the tubing 22, the resulting signal from the detector unit 10 is increased due to the higher intensity of incident light. By moving the detector unit 10 further away from the tubing 22, the resulting electrical signal is diminished but the effects of small nonuniformities in the light transmission through the tubing 22 (such as caused by a fleck of dirt on the fuel line) are reduced. In the experimental set-up, the detector unit 10 was pressed flush against the fuel line tubing 22 so as to achieve the maximized signal. However, in an automotive environment these concerns must be optimized and may require different placement of the detector unit 10 within its retaining plate 24 or use of a non-imaging reflective light concentrator or diffuser.

A schematic diagram of the actual measurement system used with the alcohol sensor of this invention is shown in FIG. 5. Specifically, a dual element operation-amplifier (op-amp) 32 is used to detect the signals from the thermopiles 11a, 11b, 12a and 12b. The thermopiles 11a, 11b, 12a and 12b are paired in series so that each pair's output voltages subtract, as indicated in FIG. 5 and in accordance with the above formula for the ratio R. As such, light-detecting thermopile 12a would be paired with ambient temperature-detecting thermopile 11a, with the paired voltage output being the difference in the individual voltage outputs of the thermopiles 12a and 11a. The same would be true for the pair consisting of light-detecting thermopile 12b and ambient temperature-detecting thermopile 11b. As noted above, the overall output signal of each thermopile pair 12a, 11a and 12b, 11b would have the influence of the ambient temperature drift subtracted out.

The op-amp 32 amplifies the output signal of each pair and relays the amplified signal to a suitable controller 34 to determine the ratio R between the two wavelengths which corresponds to the alcohol concentration in the fuel. In practice, the controller would preferably be a 0 to 5 Volt, 8 bit analog-to-digital (a-d) converter, as is available in an engine control module (ECM). Because the maximum anticipated output from the thermopiles 11a, 11b, 12a and 12b is approximately 20 mV, the preferred op-amp 32 would amplify the signal of each thermopile pair by 32 with the present invention include ensuring that the variation of the amplifier gain vs the ambient temperature is the same, while also reducing the number of components used.

In the preferred mode of operation, the controller 34 samples the voltage outputs of the op-amp 32 at a rate of once every 28 milliseconds. This cycle time corresponds to the response time for the thermopiles 11a, 11b, 12a and 12b. Accordingly, the controller 34 can sample at any time and as many times as instructed, but the accuracy of the response from the thermopiles 11a, 11b, 12a and 12b will be influenced by the light or temperature detected in the previous 28 milliseconds. If desired, the output signals of the op-amp 32 could be electrically integrated to slow down the time response. It is foreseeable that suitable results could be achieved even with cycle times as great as about 6 seconds.

Because the light source 18 is emitting light continuously through the fuel mixture within the fuel line 22 and sampling is occurring almost continuously by the controller 34, any time difference between the measurements by the two pairs of thermopiles 11a, 11b, 12a and 12b will be inconsequential to the resulting ratio of absorbances. Once these signals for the two different wavelengths are obtained, the ratio of the amounts of absorption by the alcohol/gasoline fuel mixture at both wavelengths is computed. The concentration of alcohol in the fuel is then determined from standard absorption data at a particular fuel temperature.

During continuous operation, broad band background noise and signal drift were observed from each thermopile detector 12a and 12b, which accordingly limits the accuracy of the resulting measurements. Experiments showed that some of the signal drift was associated with changes in light output from the light bulb 18. This drift is essentially eliminated by taking the ratio of the signals from the two light detecting thermopiles 12a and 12b. Also, since each thermopile 12a and 12b essentially measures a temperature difference between itself and the ambient conditions, a constant drift in ambient temperature produces an added constant output voltage, even in the absence of incident infrared radiation to the thermopiles 12a and 12b. However, as noted previously, the influence of the ambient temperature drifts in the thermopiles 12a and 12b are eliminated by employing the ambient temperature-detecting thermopiles 11a and 11b to specifically sense this form of signal noise.

It is also to be noted that a change in filament temperature within the light bulb 18 will in principle lead to a change in the measured ratio of intensities for a fixed alcohol content. Such a change, if it were to occur, say as the bulb 18 ages, would be a source of long term drift because of a change in its "color temperature", which refers to how the relative emission at different wavelengths changes as the temperature of the light source 18 changes. For example, at 2000K, the filament emits light with nearly equal intensity at the first wavelength centered about 1.3 micrometers and at the second wavelength centered about 1.5 micrometers, while at 2500K the intensity is around 13% greater at 1.3 micrometers than at 1.5 micrometers. Thus, a large temperature change within the light source 18 could lead to intolerable errors in the ratios of the signals at the two wavelengths. Experimentally, we have determined that changes in the lamp intensity of about 15% at a wavelength of about 1.5 micrometers result in changes in the ratio of detected intensities of around one percent. Therefore, bulb intensity must be kept constant to within about 10%. The simplest approach for accomplishing this was to keep the current through the light bulb 18 constant. This maintains the color temperature of the light bulb 18 as constant so long as the filament within the light bulb 18 is not damaged. Alternative means for accomplishing this would include using a silicon detector in a feed back circuit to maintain constant bulb brightness, or by using a reference filter that passes light in two bands, one greater than 1.5 micrometers, the other less than 1.5 micrometers, so that the resulting color temperature matches the 1.5 micrometer optical filter.

In addition, the alcohol sensor of this invention is equally suitable for use with an alcohol/gasoline fuel mixture which contains either ethanol or methanol. The ratios of the absorption coefficients for ethanol and methanol, are dependent upon the presence of the same O—H bonds within the molecules.

These ratios are linearly related to the concentration of either alcohol within the fuel mixture. Therefore, the alcohol sensor of this invention is capable of widespread use with various fuel mixtures.

Therefore, the alcohol sensor of this invention measures the alcohol concentration within a fuel mixture by determining the relative infrared absorbances at two particular wavelengths by the fuel mixture. The sensor includes a first pair of thermopile detectors which are disposed so as to receive the emitted light beam at each wavelength after it has been transmitted through the alcohol/gasoline fuel mixture, and a second pair of thermopile detectors which are disposed adjacent the first pair so as to detect the drift in ambient temperature of the first pair of detectors. The first thermopile of the first pair determines the amount of light absorbance by the fuel mixture at a first wavelength, and similarly, the second thermopile of the first pair determines the amount of light absorbance by the fuel mixture at the second wavelength. Accordingly each thermopile in the first pair generates a temperature rise due to the amount of incident light received.

Correspondingly, the second pair of thermopiles detects the drift in ambient temperature of the substrate in which all four thermopiles reside. The ambient temperature influence on the output voltages of the first pair of thermopiles can then be eliminated prior to taking the ratio between the absorbances at the first and second wavelengths. Once the temperature-adjusted signals at the two wavelengths are obtained, the ratio between the amounts of absorption by the alcohol/gasoline fuel mixture at both wavelengths is computed and the concentration of alcohol in the fuel is determined.

This alcohol sensor provides several particularly advantageous features. Firstly, there is no need to periodically switch the light source 18 between a relatively high power and a relatively low power to alleviate any drifts in the resulting signal due to ambient temperature changes. Ambient temperature effects are substantially eliminated since ambient temperature drift is detected closely adjacent to both of the light-detecting thermopiles and subsequently eliminated from the absorption ratio. Moreover, ambient temperature effects will be essentially identical for all four of the thermopile detectors in that they are extremely small and are mounted on a much larger chip which serves as a heat sink. Secondly, the cycle time of the sensor is significantly reduced so as to improve the sensor's ability to detect nearly instantaneous variances in the composition of the fuel mixture.

Furthermore, if any component of the sensor degrades, the degradation will equally affect both measurements and since a ratio between the two measurements is the ultimate parameter being measured, the degradation effects will essentially cancel. Also, since a light bulb is utilized as the light source, the spectral output of the light bulb is independent of local temperature. Lastly, the number of components and therefore the complexity of the sensor is minimal which thereby lends itself for widespread use including automotive applications.

In addition, there are several potential applications envisioned for this type of infrared sensing device. For example, many properties of normal gasoline fuel, such as the temperature by which half of the gasoline has boiled, aromatic content or octane number, are correlated to the infrared spectra of the fuel and could therefore be determined. In some instances, measurements at more than just two wavelengths may be required. Also, this infrared sensing device could be used to determine the composition of any absorbing medium within the automotive environment. Infrared detection with this sensor could also be used to detect water on the windshield of the automobile so as to instruct the windshield wipers to swipe across the windshield.

Therefore, while our invention has been described in terms of a preferred embodiment, it is apparent that other forms could be readily adopted by one skilled in the art, such as those variations described above or such as the incorporation of fiber optics within the sensor. Accordingly, the scope of the invention is to be limited only by the following claims.

The embodiments of the invention in which an exclusive property or privilege is claimed are defined as follows:

1. A sensing device for determining the alcohol content of an alcohol/gasoline fuel mixture during the operation of an engine, said sensing device comprising:
    a light source emitting a light beam containing at least a first and a second wavelength within the near-infrared spectrum, said light beam being continuously transmitted at a substantially constant intensity through the alcohol/gasoline fuel mixture during the operation of the engine;
    first and second detectors which are disposed so as to continuously receive said light beam after its transmission through the alcohol/gasoline fuel mixture, said first detector producing an output corresponding to a first amount of absorption by the alcohol/gasoline fuel mixture at said first wavelength, and said second detector producing an output corresponding to a second amount of absorption by the alcohol/gasoline fuel mixture at said second wavelength;
    detector means disposed adjacent said first and second detectors so as to continuously produce an output corresponding to a drift in ambient temperature of said first and second detectors, said detector means being shielded from said light source to substantially prevent said detector means from receiving said light beam;
    means for measuring said outputs from said first and second detectors and said detector means; and
    computational means for determining, from said outputs, the difference between said outputs of said first detector and said detector means and the difference between said outputs of said second detector and said detector means, the ratio of said differences being a ratio of said first and second absorbances by the alcohol/gasoline fuel mixture at said first and said second wavelengths, such that said ratio of absorbances provides an output indicative of the alcohol content within the alcohol/gasoline mixture during the operation of the engine.

2. A sensing device for determining the alcohol content of an alcohol/gasoline fuel mixture as recited in claim 1, wherein said detector means comprises third and fourth detectors, said third detector corresponding to said first detector and said fourth detector corresponding to said second detector.

3. A sensing device for determining the alcohol content of an alcohol/gasoline fuel mixture as recited in claim 2, wherein said first, second, third and fourth detectors are thermopile-type detectors and each of said thermopile-type detectors generates a predetermined voltage corresponding to an increase in their temperature, said increase in temperature being caused by incidence of said light beam at said first and second wavelengths on the surface of each of said corresponding first and second detectors respectively, said increase in temperature being caused by said drift in ambient temperature of each of said corresponding third and fourth detectors.

4. A sensing device for determining the alcohol content of an alcohol/gasoline fuel mixture as recited in claim 1 wherein said first wavelength is approximately 1.3 micrometers and said second wavelength is approximately 1.5 micrometers.

5. A sensing device for determining the alcohol content of an alcohol/gasoline mixture which is provided via a fuel carrying line to an internal combustion engine for operation of that engine, comprising:
    means for measuring the temperature of the alcohol/gasoline mixture;
    a light source emitting a light beam containing at least a first and a second wavelength within the near-infrared spectrum, said light beam being continuously transmitted at a substantially constant intensity through the alcohol/gasoline mixture within the fuel carrying line during the operation of the engine;
    first and second thermopile-type detectors disposed so as to continuously receive said emitted light beam after its transmission through the alcohol/gasoline mixture within the fuel carrying line, said first detector being optically filtered to receive a band of wavelengths centered about said first wavelength so as to produce an output corresponding to a first amount of absorbance by the alcohol/gasoline mixture at said first wavelength, and said second detector being optically filtered to receive a band of wavelengths centered about said second wavelength which does not overlap said band centered about said first wavelength so as to produce an output corresponding to a second amount of absorbance by the alcohol/gasoline fuel mixture at said second wavelength;
    third and fourth thermopile-type detectors disposed adjacent said first and second detectors such that each said third and fourth thermopile-type detectors continuously produce an output corresponding to a drift in ambient temperature of a corresponding one of said first and second detectors, said third and fourth detector being shielded from said light source to substantially prevent said third and fourth detectors from receiving said light beam, said third detector corresponding to said first detector and said fourth detector corresponding to said second detector;
    means for measuring said outputs from each of said first, second, third and fourth thermopile-type detectors; and
    computational means for determining, from said outputs, the difference between said outputs of said first and third detectors and the difference between said outputs of said second and fourth detectors, the ratio of said differences being a ratio of said first and second absorbances by the alcohol/gasoline fuel mixture at said first and said second wavelength, wherein said ratio (R) is equal to $(V_1-V_3)/(V_2-V_4)$, with $V_1$ and $V_2$ being said outputs by said first and second detectors sensing at said first and second wavelengths, respectively, and $V_3$ and $V_4$ being said outputs by said third and fourth detectors sensing said drift in ambient temperature;

such that said ratio of absorbances when considered with said temperature of the alcohol/gasoline mixture is indicative of the alcohol content within the alcohol/gasoline mixture during the operation of the engine.

6. A sensing device for determining the alcohol content of an alcohol/gasoline mixture as recited in claim 5 wherein at said first wavelength, the alcohol is significantly more absorbing than the gasoline component of the alcohol/gasoline mixture and at said second wavelength, the alcohol and gasoline components are both essentially non-absorbing.

7. A sensing device for determining the alcohol content of an alcohol/gasoline mixture as recited in claim 6 wherein said first wavelength is approximately 1.3 micrometers and said second wavelength is approximately 1.5 micrometers.

8. A sensing device for determining the alcohol content of an alcohol/gasoline mixture as recited in claim 7 wherein said bands are about 0.2 micrometers wide centered about each said first and second wavelengths.

9. A sensing device for determining the alcohol content of an alcohol/gasoline mixture containing up to about 85% by volume of alcohol, which is provided via a fuel carrying line to an internal combustion engine for operation of that engine, comprising:

means for measuring the temperature of the alcohol/gasoline mixture;

a light source emitting a light beam containing at least a first and a second wavelength within the near-infrared spectrum, wherein at said first wavelength, the alcohol is significantly more absorbing than the gasoline component of the alcohol/gasoline mixture and at said second wavelength, the alcohol and gasoline components are both essentially non-absorbing, said light beam being continuously transmitted at a substantially constant intensity through the alcohol/gasoline mixture over a single optical path of predetermined length through the fuel carrying line during the operation of the engine;

first and second thermopile-type detectors disposed so as to continuously receive said light beam after its transmission through the alcohol/gasoline mixture within the fuel carrying line, said first detector being optically filtered to receive a spectral band of wavelengths centered about said first wavelength so as to produce an output corresponding to a first amount of absorbance by the alcohol/gasoline mixture at said first wavelength, and said second detector being optically filtered to receive a spectral band of wavelengths centered about said second wavelength which does not overlap said band centered around said first wavelength so as to produce an output corresponding to a second amount of absorbance by the alcohol/gasoline mixture at said second wavelength;

third and fourth thermopile-type detectors disposed adjacent said first and second detectors such that each said third and fourth thermopile-type detectors produces an output corresponding to a drift in ambient temperature of a corresponding one of said first and second detectors, said third and fourth detectors being shielded by opaque screens from said light source to substantially prevent said third and fourth detectors from receiving said light beam, said third detector corresponding to said first detector and said fourth detector corresponding to said second detector;

means for measuring said outputs from each of said first, second, third and fourth thermopile-type detectors; and computational means for determining, from said outputs, the difference between said outputs of said first and third detectors and the difference between said outputs of said second and fourth detectors, the ratio of said differences being a ratio of said first and second absorbances by the alcohol/gasoline fuel mixture at said first and said second wavelength, wherein said ratio (R) is equal to $(V_1-V_3)/(V_2-V_4)$, with $V_1$ and $V_2$ being said outputs by said first and second detectors sensing at said first and second wavelengths, respectively, and $V_3$ and $V_4$ being said outputs by said third and fourth detectors sensing at said ambient temperature;

such that said ratio of absorbances when considered with said temperature of the alcohol/gasoline mixture is indicative of the alcohol content within the alcohol/gasoline mixture during the operation of the engine.

10. A sensing device for determining the alcohol content of an alcohol/gasoline mixture as recited in claim 9 wherein said first wavelength is approximately 1.3 micrometers and said second wavelength is approximately 1.5 micrometers.

11. A sensing device for determining the alcohol content of an alcohol/gasoline mixture as recited in claim 10 wherein said spectral bands are about 0.2 micrometers wide centered about each said first and second wavelengths.

12. A sensing device for determining the alcohol content of an alcohol/gasoline mixture as recited in claim 9 wherein said predetermined optical path length ranges between one to three millimeters.

13. A sensing device for determining the alcohol content of an alcohol/gasoline mixture which is provided via a fuel carrying line to an internal combustion engine for operation of that engine, said sensing device including means for measuring the temperature of the alcohol/gasoline mixture, a light source emitting a light beam containing at least a first and a second wavelength within the near-infrared spectrum, said light beam being continuously transmitted at a substantially constant intensity through the alcohol/gasoline mixture within the fuel carrying line during the operation of the engine, first and second thermopile-type detectors disposed so as to continuously receive said emitted light beam after its transmission through the alcohol/gasoline mixture within the fuel carrying line, said first detector being optically filtered to receive a band of wavelengths centered about said first wavelength so as to produce an output corresponding to a first amount of absorbance by the alcohol/gasoline mixture at said first wavelength, and said second detector being optically filtered to receive a band of wavelengths centered about said second wavelength which does not overlap said band centered about said first wavelength so as to produce an output corresponding to a second amount of absorbance by the alcohol/gasoline mixture at said second wavelength, wherein the improvement comprises;

third and fourth thermopile-type detectors disposed adjacent to said first and second detectors such that each said third and fourth thermopile-type detectors produces an output corresponding to a drift in ambient temperature of a corresponding one of said first and second detectors, said third and fourth detectors being shielded from said light source to substantially prevent said third and fourth detectors from receiving said light beam, said third detector corresponding to said first detector and said fourth detector corresponding to said second detector;

means for separately measuring said outputs from each of said first, second, third and fourth thermopile-type detectors; and computational means for determining, from said outputs, the difference between said outputs of said first and third detectors and the difference between said outputs of said second and fourth detectors, the ratio of said differences being a ratio of said first and second absorbances by the alcohol/gasoline fuel mixture at said first and said second wavelength, wherein said ratio (R) is equal to $(V_1-V_3)/(V_2-V_4)$, with $V_1$ and $V_2$ being said outputs by said first and second detectors sensing at said first and second wavelengths, respectively, and $V_3$ and $V_4$ being said outputs by said third and fourth detectors sensing at said ambient temperature;

such that said ratio of absorbances when considered with said temperature of the alcohol/gasoline mixture is indicative of the alcohol content within the alcohol/gasoline mixture during the operation of the engine.

14. A method for determining the alcohol content of an alcohol/gasoline mixture containing up to about 85% by volume of alcohol, which is provided via a fuel carrying line to an internal combustion engine for operation of that engine, comprising the following steps:

continuously emitting a light beam at a substantially constant intensity from a light source during the operation of the engine, said light beam containing at least a first and a second wavelength within the near-infrared spectrum, wherein at said first wavelength, the alcohol is significantly more absorbing than the gasoline component of the mixture and at said second wavelength, the alcohol and gasoline components are both essentially non-absorbing, said light beam being transmitted through the alcohol/gasoline mixture over a single optical path of predetermined length through the fuel carrying line;

continuously detecting at a first and second detector said emitted light beam after transmission through the alcohol/gasoline mixture within the fuel carrying line, said first detector being optically filtered to receive a spectral band of wavelengths centered about said first wavelength so as to determine a first amount of absorbance by the alcohol/gasoline mixture at said first wavelength, and said second detector being optically filtered to receive a spectral band of wavelengths centered about said second wavelength which does not overlap said band centered around said first wavelength so as to determine a second amount of absorbance by the alcohol/gasoline mixture at said second wavelength, said first and second detectors each generating an output voltage proportional to the sum of the incident light it receives at each of said wavelengths and an ambient temperature;

continuously detecting said ambient temperature with a third and fourth thermopile-type detectors disposed adjacent to said first and second detectors such that each said third and fourth thermopile-type detectors produces an output voltage corresponding to a drift in said ambient temperature of a corresponding one of said first and second detectors, said third and fourth detector being shielded by opaque screens from said light source to substantially prevent said third and fourth detectors from receiving said light beam, said third detector corresponding to said first detector and said fourth detector corresponding to said second detector;

measuring said output voltage from each of said first, second, third and fourth detectors; and computing from said output voltages, the difference between said output voltages of said first and third detectors and the difference between said output voltages of said second and fourth detectors, the ratio of said differences being a ratio of said first and second absorbances by the alcohol/gasoline fuel mixture at said first and said second wavelength, wherein said ratio (R) is equal to $(V_1-V_3)/(V_2-V_4)$, with $V_1$ and $V_2$ being said output voltages by said first and second detectors sensing at said first and second wavelengths, respectively, and $V_3$ and $V_4$ being said output voltages by said third and fourth detectors sensing said drift in said ambient temperature;

such that said ratio of absorbances is indicative of the alcohol content within the alcohol/gasoline mixture.

15. A method for determining the alcohol content of an alcohol/gasoline mixture as recited in claim 14 wherein said first wavelength is approximately 1.3 micrometers and said second wavelength is approximately 1.5 micrometers.

16. A method for determining the alcohol content of an alcohol/gasoline mixture as recited in claim 15 wherein said spectral bands are about 0.2 micrometers wide centered about each said first and second wavelengths.

17. A method for determining the alcohol content of an alcohol/gasoline mixture as recited in claim 14 wherein said predetermined optical path length ranges between one to three millimeters.

* * * * *